United States Patent
Ehrenreich et al.

(10) Patent No.: US 8,076,529 B2
(45) Date of Patent: *Dec. 13, 2011

(54) EXPANDABLE MEMBER FORMED OF A FIBROUS MATRIX FOR INTRALUMINAL DRUG DELIVERY

(75) Inventors: Kevin J. Ehrenreich, San Francisco, CA (US); Richard R. Newhauser, Redwood City, CA (US); Randolf von Oepen, Los Altos Hills, CA (US); John Stankus, Campbell, CA (US)

(73) Assignee: Abbott Cardiovascular Systems, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/238,627

(22) Filed: Sep. 26, 2008

(65) Prior Publication Data

US 2010/0081992 A1 Apr. 1, 2010

(51) Int. Cl.
*A61F 13/15* (2006.01)
*A61F 13/20* (2006.01)
*A61M 31/00* (2006.01)
*A61M 37/00* (2006.01)
*A61M 29/00* (2006.01)

(52) U.S. Cl. ............... 604/367; 604/96.01; 604/103.08; 604/286

(58) Field of Classification Search ............ 604/103.08, 604/96.01, 103.06, 101.01, 101.04, 286, 604/365–368
See application file for complete search history.

(56) References Cited

U.S. PATENT DOCUMENTS

| | | | |
|---|---|---|---|
| 4,564,014 A | 1/1986 | Fogarty et al. |
| 4,878,906 A | 11/1989 | Lindemann et al. |
| 4,959,074 A | 9/1990 | Halpern et al. |
| 4,990,357 A | 2/1991 | Karakelle et al. |
| 5,026,607 A | 6/1991 | Kiezulas |
| 5,049,131 A | 9/1991 | Deuss |
| 5,061,273 A | 10/1991 | Yock |
| 5,092,841 A | 3/1992 | Spears |

(Continued)

FOREIGN PATENT DOCUMENTS

DE 10244847 4/2004

(Continued)

OTHER PUBLICATIONS

U.S. Appl. No. 12/237,998, filed Sep. 25, 2008, von Oepen et al.

(Continued)

*Primary Examiner* — Nicholas D Lucchesi
*Assistant Examiner* — Rebecca E Eisenberg
(74) *Attorney, Agent, or Firm* — Randy Shen

(57) ABSTRACT

An intraluminal catheter device having an expandable member formed of a matrix of fiber elements with a therapeutic agent incorporated therein. The therapeutic agent can be coated on the fiber elements in a co-axial configuration. The fiber elements may also have a second coating including a protective substance surrounding the therapeutic agent. The matrix of fiber elements can be formed by electrospinning. A process of delivering a therapeutic agent to a target site includes providing an intraluminal catheter device having an expandable member formed of a matrix of fiber elements, the expandable member having a therapeutic agent dispersed therein, and advancing the catheter device at a desired treatment site. Once at the desired treatment site, fluid is introduced into the inflation lumen to expand the expandable member from a first profile to a second profile, and the therapeutic agent is delivered to the desired treatment site.

31 Claims, 4 Drawing Sheets

U.S. PATENT DOCUMENTS

| | | |
|---|---|---|
| 5,102,402 A | 4/1992 | Dror et al. |
| 5,272,012 A | 12/1993 | Opolski |
| 5,295,978 A | 3/1994 | Fan et al. |
| 5,304,121 A | 4/1994 | Sahatjian |
| 5,324,261 A | 6/1994 | Amundson et al. |
| 5,370,614 A | 12/1994 | Amundson et al. |
| 5,380,299 A | 1/1995 | Fearnot et al. |
| 5,456,694 A | 10/1995 | Marin et al. |
| 5,458,573 A | 10/1995 | Summers |
| 5,458,615 A | 10/1995 | Klemm et al. |
| 5,476,476 A | 12/1995 | Hillstead |
| 5,507,768 A | 4/1996 | Lau et al. |
| 5,549,551 A | 8/1996 | Peacock, III et al. |
| 5,562,922 A | 10/1996 | Lambert |
| 5,578,340 A | 11/1996 | Ogawa et al. |
| 5,588,962 A | 12/1996 | Nicholas et al. |
| 5,609,629 A | 3/1997 | Fearnot et al. |
| 5,620,738 A | 4/1997 | Fan et al. |
| 5,674,192 A | 10/1997 | Sahatjian et al. |
| 5,685,847 A | 11/1997 | Barry |
| 5,707,385 A | 1/1998 | Williams |
| 5,728,420 A | 3/1998 | Keogh |
| 5,733,925 A | 3/1998 | Kunz et al. |
| 5,756,144 A | 5/1998 | Wolff et al. |
| 5,766,158 A | 6/1998 | Opolski |
| 5,782,855 A | 7/1998 | Lau et al. |
| 5,820,917 A | 10/1998 | Tuch |
| 5,820,918 A | 10/1998 | Ronan et al. |
| 5,821,343 A | 10/1998 | Keogh |
| 5,824,049 A | 10/1998 | Ragheb et al. |
| 5,837,313 A | 11/1998 | Ding et al. |
| 5,843,033 A | 12/1998 | Ropiak |
| 5,843,089 A | 12/1998 | Sahatjian et al. |
| 5,860,954 A | 1/1999 | Ropiak |
| 5,868,719 A | 2/1999 | Tsukernik |
| 5,891,506 A | 4/1999 | Keogh |
| 5,893,840 A | 4/1999 | Hull et al. |
| 5,900,246 A | 5/1999 | Lambert |
| 5,914,182 A | 6/1999 | Drumheller |
| 5,925,552 A | 7/1999 | Keogh et al. |
| 5,928,916 A | 7/1999 | Keogh |
| 5,945,319 A | 8/1999 | Keogh |
| 5,954,706 A | 9/1999 | Sahatjian |
| 5,977,163 A | 11/1999 | Li et al. |
| 5,980,972 A | 11/1999 | Ding |
| 5,981,568 A | 11/1999 | Kunz et al. |
| 6,010,521 A | 1/2000 | Lee et al. |
| 6,017,741 A | 1/2000 | Keogh |
| 6,033,719 A | 3/2000 | Keogh |
| 6,039,721 A | 3/2000 | Johnson et al. |
| 6,048,620 A | 4/2000 | Zhong |
| 6,050,980 A | 4/2000 | Wilson |
| 6,074,659 A | 6/2000 | Kunz et al. |
| 6,093,463 A | 7/2000 | Thakrar |
| 6,096,726 A | 8/2000 | Opolski |
| 6,099,562 A | 8/2000 | Ding et al. |
| 6,099,926 A | 8/2000 | Thakrar |
| 6,106,889 A | 8/2000 | Beavers et al. |
| 6,107,416 A | 8/2000 | Patnaik et al. |
| 6,110,590 A | 8/2000 | Zarkoob et al. |
| 6,129,705 A | 10/2000 | Grantz |
| 6,143,037 A | 11/2000 | Goldstein et al. |
| 6,146,358 A | 11/2000 | Rowe |
| 6,200,257 B1 | 3/2001 | Winkler |
| 6,214,901 B1 | 4/2001 | Chudzik et al. |
| 6,218,016 B1 | 4/2001 | Tedeschi et al. |
| 6,248,127 B1 | 6/2001 | Shah et al. |
| 6,254,921 B1 | 7/2001 | Chappa et al. |
| 6,264,633 B1 | 7/2001 | Knorig |
| 6,268,390 B1 | 7/2001 | Kunz |
| 6,270,831 B2 | 8/2001 | Kumar et al. |
| 6,280,411 B1 | 8/2001 | Lennox |
| 6,303,179 B1 | 10/2001 | Koulik et al. |
| 6,306,166 B1 | 10/2001 | Barry et al. |
| 6,306,421 B1 | 10/2001 | Kunz et al. |
| 6,335,029 B1 | 1/2002 | Kamath et al. |
| 6,364,856 B1 | 4/2002 | Ding et al. |
| 6,364,893 B1 | 4/2002 | Sahatjian et al. |
| 6,368,658 B1 | 4/2002 | Schwarz et al. |
| 6,369,039 B1 | 4/2002 | Palasis et al. |
| 6,379,691 B1 | 4/2002 | Tedeschi et al. |
| 6,382,526 B1 | 5/2002 | Reneker et al. |
| 6,395,208 B1 | 5/2002 | Herweck et al. |
| 6,409,716 B1 | 6/2002 | Sahatjian et al. |
| 6,419,692 B1 | 7/2002 | Yang et al. |
| 6,443,942 B2 | 9/2002 | Van Antwerp et al. |
| 6,447,835 B1 | 9/2002 | Wang et al. |
| 6,461,666 B2 | 10/2002 | Park |
| 6,475,434 B1 | 11/2002 | Darouiche |
| 6,491,938 B2 | 12/2002 | Kunz et al. |
| 6,491,965 B1 | 12/2002 | Berry et al. |
| 6,506,408 B1 | 1/2003 | Palasis |
| 6,506,411 B2 | 1/2003 | Hunter et al. |
| 6,515,009 B1 | 2/2003 | Kunz et al. |
| 6,517,888 B1 | 2/2003 | Weber |
| 6,520,425 B1 | 2/2003 | Reneker |
| 6,521,283 B1 | 2/2003 | Yianni |
| 6,524,274 B1 | 2/2003 | Rosenthal et al. |
| 6,537,194 B1 | 3/2003 | Winkler |
| 6,544,221 B1 | 4/2003 | Kokish et al. |
| 6,544,223 B1 | 4/2003 | Kokish |
| 6,544,544 B2 | 4/2003 | Hunter et al. |
| 6,545,097 B2 | 4/2003 | Pinchuk et al. |
| 6,555,157 B1 | 4/2003 | Hossainy |
| 6,555,225 B1 | 4/2003 | Yoshioka et al. |
| 6,571,771 B2 | 6/2003 | Doering et al. |
| 6,579,539 B2 | 6/2003 | Lawson et al. |
| 6,589,546 B2 | 7/2003 | Kamath et al. |
| 6,596,699 B2 | 7/2003 | Zamora et al. |
| 6,616,650 B1 | 9/2003 | Rowe |
| 6,617,142 B2 | 9/2003 | Keogh et al. |
| 6,627,246 B2 | 9/2003 | Mehta et al. |
| 6,638,563 B2 | 10/2003 | McGee et al. |
| 6,641,611 B2 | 11/2003 | Jayaraman |
| 6,645,547 B1 | 11/2003 | Shekalim et al. |
| 6,649,030 B1 | 11/2003 | Tesar |
| 6,656,156 B2 | 12/2003 | Yang et al. |
| 6,663,881 B2 | 12/2003 | Kunz et al. |
| 6,669,980 B2 | 12/2003 | Hansen |
| 6,673,453 B2 | 1/2004 | Beavers et al. |
| 6,676,987 B2 | 1/2004 | Zhong et al. |
| 6,683,062 B2 | 1/2004 | Opolski |
| 6,695,809 B1 | 2/2004 | Lee |
| 6,695,992 B2 | 2/2004 | Reneker |
| 6,706,408 B2 | 3/2004 | Jelle |
| 6,713,119 B2 | 3/2004 | Hossainy et al. |
| 6,719,991 B2 | 4/2004 | Darouiche et al. |
| 6,730,349 B2 | 5/2004 | Schwarz et al. |
| 6,733,819 B2 | 5/2004 | Burkett et al. |
| 6,737,447 B1 | 5/2004 | Smith et al. |
| 6,743,462 B1 | 6/2004 | Pacetti |
| 6,743,463 B2 | 6/2004 | Weber et al. |
| 6,743,521 B2 | 6/2004 | Hubbell et al. |
| 6,753,071 B1 | 6/2004 | Pacetti |
| 6,753,454 B1 | 6/2004 | Mello et al. |
| 6,764,709 B2 | 7/2004 | Flanagan |
| 6,776,771 B2 | 8/2004 | van Moorlegem et al. |
| 6,793,960 B1 | 9/2004 | Michal et al. |
| 6,818,247 B1 | 11/2004 | Chen et al. |
| 6,821,479 B1 | 11/2004 | Smith et al. |
| 6,821,528 B2 | 11/2004 | Scott et al. |
| 6,828,028 B1 | 12/2004 | Fukui et al. |
| 6,830,583 B2 | 12/2004 | Shah et al. |
| 6,833,153 B1 | 12/2004 | Roorda et al. |
| 6,855,366 B2 | 2/2005 | Smith et al. |
| 6,855,770 B2 | 2/2005 | Pinchuk et al. |
| 6,861,088 B2 | 3/2005 | Weber et al. |
| 6,865,810 B2 | 3/2005 | Stinson |
| 6,884,628 B2 | 4/2005 | Hubbell et al. |
| 6,887,270 B2 | 5/2005 | Miller et al. |
| 6,887,510 B2 | 5/2005 | Villareal |
| 6,890,339 B2 | 5/2005 | Sahatjian et al. |
| 6,899,731 B2 | 5/2005 | Li et al. |
| 6,904,310 B2 | 6/2005 | Knapp et al. |
| 6,918,869 B2 | 7/2005 | Shaw et al. |
| 6,918,927 B2 | 7/2005 | Bates et al. |
| 6,919,100 B2 | 7/2005 | Narayanan |

| | | |
|---|---|---|
| 6,921,811 B2 | 7/2005 | Zamora et al. |
| 6,923,996 B2 | 8/2005 | Epstein et al. |
| 6,926,919 B1 | 8/2005 | Hossainy et al. |
| 6,939,320 B2 | 9/2005 | Lennox |
| 6,953,466 B2 | 10/2005 | Palasis et al. |
| 6,954,977 B2 | 10/2005 | Maguire et al. |
| 6,991,617 B2 | 1/2006 | Hektner et al. |
| 6,994,689 B1 | 2/2006 | Zadno-Azizi et al. |
| 7,008,667 B2 | 3/2006 | Chudzik et al. |
| 7,014,913 B2 | 3/2006 | Pacetti |
| 7,048,714 B2 | 5/2006 | Richter |
| 7,048,962 B2 | 5/2006 | Shekalim et al. |
| 7,060,051 B2 | 6/2006 | Palasis |
| 7,066,904 B2 | 6/2006 | Rosenthal et al. |
| 7,083,644 B1 | 8/2006 | Moroni |
| 7,087,135 B2 | 8/2006 | Dillon |
| 7,087,263 B2 | 8/2006 | Hossainy et al. |
| 7,105,175 B2 | 9/2006 | Schwarz |
| 7,108,684 B2 | 9/2006 | Farnan |
| 7,115,299 B2 | 10/2006 | Kokish |
| 7,122,356 B2 | 10/2006 | Keogh et al. |
| RE39,438 E | 12/2006 | Shah et al. |
| 7,163,334 B2 | 1/2007 | Chase et al. |
| 7,182,779 B2 | 2/2007 | Acosta et al. |
| 7,198,855 B2 | 4/2007 | Liebmann-Vinson et al. |
| 7,201,935 B1 | 4/2007 | Claude et al. |
| 7,208,190 B2 | 4/2007 | Verlee et al. |
| 7,220,491 B2 | 5/2007 | Rouns et al. |
| 7,226,612 B2 | 6/2007 | Sohier et al. |
| 7,241,455 B2 | 7/2007 | Richard |
| 7,241,478 B2 | 7/2007 | McNeish et al. |
| 7,258,891 B2 | 8/2007 | Pacetti et al. |
| 7,267,847 B2 | 9/2007 | Karamuk |
| 7,279,175 B2 | 10/2007 | Chen et al. |
| 7,326,433 B2 | 2/2008 | Stenzel |
| 7,335,391 B1 | 2/2008 | Pacetti |
| 7,345,053 B2 | 3/2008 | Garvey |
| 7,357,940 B2 | 4/2008 | Richard et al. |
| 7,364,585 B2 | 4/2008 | Weber |
| 7,364,768 B2 | 4/2008 | Rypacek et al. |
| 7,381,418 B2 | 6/2008 | Richard |
| 7,387,810 B2 | 6/2008 | Hossainy |
| 7,390,525 B2 | 6/2008 | Epstein et al. |
| 7,398,118 B2 | 7/2008 | Knapp et al. |
| 7,402,172 B2 | 7/2008 | Chin et al. |
| 7,402,329 B2 | 7/2008 | Pacetti et al. |
| 7,407,684 B2 | 8/2008 | Spencer et al. |
| 7,442,402 B2 | 10/2008 | Chudzik et al. |
| 7,445,792 B2 | 11/2008 | Toner et al. |
| 7,449,210 B2 | 11/2008 | Malik et al. |
| 7,455,875 B2 | 11/2008 | Weber et al. |
| 7,459,169 B2 | 12/2008 | Nilsson et al. |
| 7,462,165 B2 | 12/2008 | Ding et al. |
| 7,468,210 B1 | 12/2008 | Zamora |
| 7,470,469 B1 | 12/2008 | Michal et al. |
| 7,476,246 B2 | 1/2009 | Pathak |
| 7,482,034 B2 | 1/2009 | Boulais |
| 7,485,334 B2 | 2/2009 | Kerrigan |
| 2001/0026834 A1 | 10/2001 | Chappa et al. |
| 2002/0084178 A1 | 7/2002 | Dubson et al. |
| 2003/0064965 A1 | 4/2003 | Richter |
| 2003/0065355 A1 | 4/2003 | Weber |
| 2003/0077253 A1 | 4/2003 | Palasis |
| 2003/0100829 A1 | 5/2003 | Zhong et al. |
| 2003/0104030 A1* | 6/2003 | Igaki et al. .................... 424/426 |
| 2003/0206960 A1 | 11/2003 | Iversen et al. |
| 2003/0207019 A1 | 11/2003 | Shekalim et al. |
| 2003/0207907 A1 | 11/2003 | Iversen et al. |
| 2003/0236513 A1 | 12/2003 | Schwarz et al. |
| 2003/0236514 A1 | 12/2003 | Schwarz |
| 2004/0018296 A1 | 1/2004 | Castro et al. |
| 2004/0034337 A1 | 2/2004 | Boulais et al. |
| 2004/0043068 A1 | 3/2004 | Tedeschi et al. |
| 2004/0058084 A1 | 3/2004 | Shekalim et al. |
| 2004/0073284 A1 | 4/2004 | Bates et al. |
| 2004/0087984 A1 | 5/2004 | Kupiecki et al. |
| 2004/0098089 A1 | 5/2004 | Weber |
| 2004/0098106 A1 | 5/2004 | Williams et al. |
| 2004/0106987 A1 | 6/2004 | Palasis et al. |
| 2004/0126400 A1 | 7/2004 | Iversen et al. |
| 2004/0224003 A1 | 11/2004 | Schultz |
| 2005/0025802 A1 | 2/2005 | Richard et al. |
| 2005/0025808 A1 | 2/2005 | Herrmann et al. |
| 2005/0027283 A1 | 2/2005 | Richard et al. |
| 2005/0037047 A1 | 2/2005 | Song |
| 2005/0037048 A1 | 2/2005 | Song |
| 2005/0064005 A1 | 3/2005 | Dinh et al. |
| 2005/0090891 A1 | 4/2005 | Sahatjian et al. |
| 2005/0106206 A1 | 5/2005 | Herweck et al. |
| 2005/0113687 A1 | 5/2005 | Herweck et al. |
| 2005/0163954 A1 | 7/2005 | Shaw |
| 2005/0181015 A1 | 8/2005 | Zhong |
| 2005/0182361 A1 | 8/2005 | Lennox |
| 2005/0215722 A1 | 9/2005 | Pinchunk et al. |
| 2005/0220853 A1 | 10/2005 | Dao et al. |
| 2005/0241577 A1 | 11/2005 | Shekalim et al. |
| 2005/0271701 A1 | 12/2005 | Cottone et al. |
| 2005/0278021 A1 | 12/2005 | Bates et al. |
| 2006/0008606 A1 | 1/2006 | Horn et al. |
| 2006/0013853 A1 | 1/2006 | Richard |
| 2006/0013867 A1 | 1/2006 | Richard et al. |
| 2006/0020243 A1 | 1/2006 | Speck et al. |
| 2006/0020331 A1 | 1/2006 | Bates et al. |
| 2006/0030936 A1 | 2/2006 | Weber et al. |
| 2006/0034931 A1 | 2/2006 | Hansen |
| 2006/0043650 A1 | 3/2006 | Hossainy et al. |
| 2006/0051390 A1 | 3/2006 | Schwarz |
| 2006/0073265 A1 | 4/2006 | Teichman et al. |
| 2006/0079836 A1 | 4/2006 | Holman et al. |
| 2006/0083768 A1 | 4/2006 | Labrecque et al. |
| 2006/0085023 A1 | 4/2006 | Davies et al. |
| 2006/0110209 A1 | 5/2006 | Shekalim et al. |
| 2006/0122697 A1 | 6/2006 | Shanley et al. |
| 2006/0153904 A1 | 7/2006 | Smith et al. |
| 2006/0165872 A1 | 7/2006 | Chappa et al. |
| 2006/0167407 A1 | 7/2006 | Weber et al. |
| 2006/0171981 A1 | 8/2006 | Richard et al. |
| 2006/0184112 A1* | 8/2006 | Horn et al. ................. 604/103.08 |
| 2006/0230476 A1 | 10/2006 | Atanasoska et al. |
| 2006/0280858 A1 | 12/2006 | Kokish |
| 2007/0003599 A1 | 1/2007 | Schwarz |
| 2007/0014827 A1 | 1/2007 | Larrick et al. |
| 2007/0048351 A1 | 3/2007 | Lunn |
| 2007/0172509 A1 | 7/2007 | Nguyen et al. |
| 2007/0212386 A1 | 9/2007 | Patravale et al. |
| 2007/0212388 A1 | 9/2007 | Patravale et al. |
| 2007/0212393 A1 | 9/2007 | Patravale et al. |
| 2007/0255206 A1* | 11/2007 | Reneker et al. ............. 604/96.01 |
| 2007/0259017 A1 | 11/2007 | Francis |
| 2007/0298069 A1 | 12/2007 | Bucay Couto et al. |
| 2008/0015500 A1 | 1/2008 | Herweck et al. |
| 2008/0015628 A1 | 1/2008 | Dubrul et al. |
| 2008/0021385 A1 | 1/2008 | Barry et al. |
| 2008/0027531 A1 | 1/2008 | Reneker et al. |
| 2008/0050415 A1 | 2/2008 | Atanasoska et al. |
| 2008/0050418 A1 | 2/2008 | Ranade et al. |
| 2008/0051871 A1 | 2/2008 | Tuch |
| 2008/0051881 A1 | 2/2008 | Feng et al. |
| 2008/0057102 A1 | 3/2008 | Roorda |
| 2008/0085294 A1 | 4/2008 | Freyman et al. |
| 2008/0113081 A1 | 5/2008 | Hossainy et al. |
| 2008/0118544 A1 | 5/2008 | Wang |
| 2008/0124372 A1 | 5/2008 | Hossainy et al. |
| 2008/0146489 A1 | 6/2008 | Pacetti et al. |
| 2008/0181927 A1 | 7/2008 | Zhao |
| 2008/0188825 A1 | 8/2008 | Atanasoska et al. |
| 2008/0188925 A1 | 8/2008 | Zhao |
| 2008/0195079 A1 | 8/2008 | Moore et al. |
| 2008/0206442 A1 | 8/2008 | Shekalim et al. |
| 2008/0234799 A1 | 9/2008 | Acosta et al. |
| 2008/0254297 A1 | 10/2008 | Edelman |
| 2008/0255508 A1 | 10/2008 | Wang |
| 2008/0255509 A1 | 10/2008 | Wang |
| 2008/0255510 A1 | 10/2008 | Wang |
| 2008/0264336 A1 | 10/2008 | Schwarz et al. |
| 2008/0274159 A1 | 11/2008 | Schultz |
| 2009/0011116 A1 | 1/2009 | Herweck et al. |

| | | | |
|---|---|---|---|
| 2009/0299450 A1 | 12/2009 | Johnson et al. | |
| 2010/0076377 A1 | 3/2010 | Ehrenreich et al. | |
| 2010/0076401 A1 | 3/2010 | Von Oepen et al. | |

FOREIGN PATENT DOCUMENTS

| | | |
|---|---|---|
| EP | 372088 | 6/1990 |
| EP | 519063 | 12/1992 |
| EP | 565604 | 10/1993 |
| EP | 689465 | 1/1996 |
| EP | 708671 | 5/1996 |
| EP | 712615 | 5/1996 |
| EP | 797988 | 10/1997 |
| EP | 803257 | 10/1997 |
| EP | 819011 | 1/1998 |
| EP | 826382 | 3/1998 |
| EP | 836429 | 4/1998 |
| EP | 879595 | 11/1998 |
| EP | 920843 | 6/1999 |
| EP | 932399 | 8/1999 |
| EP | 980280 | 2/2000 |
| EP | 992252 | 4/2000 |
| EP | 1007135 | 6/2000 |
| EP | 1035871 | 9/2000 |
| EP | 1037677 | 9/2000 |
| EP | 1079872 | 3/2001 |
| EP | 1140273 | 10/2001 |
| EP | 1150622 | 11/2001 |
| EP | 1159974 | 12/2001 |
| EP | 1165157 | 1/2002 |
| EP | 1220694 | 7/2002 |
| EP | 1330273 | 7/2003 |
| EP | 1339440 | 9/2003 |
| EP | 1341565 | 9/2003 |
| EP | 1343544 | 9/2003 |
| EP | 1383551 | 1/2004 |
| EP | 1447098 | 8/2004 |
| EP | 1462127 | 9/2004 |
| EP | 1539266 | 6/2005 |
| EP | 1539267 | 6/2005 |
| EP | 1562669 | 8/2005 |
| EP | 1575642 | 9/2005 |
| EP | 1610856 | 1/2006 |
| EP | 1663345 | 6/2006 |
| EP | 1666070 | 6/2006 |
| EP | 1677849 | 7/2006 |
| EP | 1683520 | 7/2006 |
| EP | 1691856 | 8/2006 |
| EP | 1695697 | 8/2006 |
| EP | 1735042 | 12/2006 |
| EP | 1750782 | 2/2007 |
| EP | 1762255 | 3/2007 |
| EP | 1800702 | 6/2007 |
| EP | 1804893 | 7/2007 |
| EP | 1832301 | 9/2007 |
| EP | 1842567 | 10/2007 |
| EP | 1857127 | 11/2007 |
| EP | 1952789 | 8/2008 |
| WO | WO9211890 | 7/1992 |
| WO | WO9211895 | 7/1992 |
| WO | WO9211896 | 7/1992 |
| WO | WO9421308 | 9/1994 |
| WO | WO 95/03083 A1 | 2/1995 |
| WO | WO9630064 | 10/1996 |
| WO | WO9639949 | 12/1996 |
| WO | WO9733552 | 9/1997 |
| WO | WO9811828 | 3/1998 |
| WO | WO9831415 | 7/1998 |
| WO | WO9908729 | 2/1999 |
| WO | WO9916500 | 4/1999 |
| WO | WO 99/27968 A2 | 6/1999 |
| WO | WO9929353 | 6/1999 |
| WO | WO9959649 | 11/1999 |
| WO | WO0010552 | 3/2000 |
| WO | WO0021584 | 4/2000 |
| WO | WO0032238 | 6/2000 |
| WO | WO0032267 | 6/2000 |
| WO | WO 00/48645 A2 | 8/2000 |
| WO | WO0045744 | 8/2000 |
| WO | WO 01/26702 A2 | 4/2001 |
| WO | WO0222198 | 3/2002 |
| WO | WO0243786 | 6/2002 |
| WO | WO0247731 | 6/2002 |
| WO | WO03002267 | 1/2003 |
| WO | WO03008005 | 1/2003 |
| WO | WO03045523 | 6/2003 |
| WO | WO03090684 | 11/2003 |
| WO | WO03092741 | 11/2003 |
| WO | WO04000380 | 12/2003 |
| WO | WO04000381 | 12/2003 |
| WO | WO2004006976 | 1/2004 |
| WO | WO2004022124 | 3/2004 |
| WO | WO2004028582 | 4/2004 |
| WO | WO2004028587 | 4/2004 |
| WO | WO2004028610 | 4/2004 |
| WO | WO2004039445 | 5/2004 |
| WO | WO2004043506 | 5/2004 |
| WO | WO2004058320 | 7/2004 |
| WO | WO2004060405 | 7/2004 |
| WO | WO2004075943 | 9/2004 |
| WO | WO 2004/091714 A2 | 10/2004 |
| WO | WO2004098671 | 11/2004 |
| WO | WO2004098697 | 11/2004 |
| WO | WO2005011766 | 2/2005 |
| WO | WO2005011767 | 2/2005 |
| WO | WO2005011768 | 2/2005 |
| WO | WO2005011772 | 2/2005 |
| WO | WO2005016399 | 2/2005 |
| WO | WO2005018501 | 3/2005 |
| WO | WO2005018606 | 3/2005 |
| WO | WO2005027994 | 3/2005 |
| WO | WO2005037339 | 4/2005 |
| WO | WO2005039664 | 5/2005 |
| WO | WO2005046747 | 5/2005 |
| WO | WO2005049021 | 6/2005 |
| WO | WO2005070008 | 8/2005 |
| WO | WO2005072651 | 8/2005 |
| WO | WO 2005/089855 A1 | 9/2005 |
| WO | WO2005079335 | 9/2005 |
| WO | WO2005079339 | 9/2005 |
| WO | WO2005079754 | 9/2005 |
| WO | WO2005097066 | 10/2005 |
| WO | WO2005098955 | 10/2005 |
| WO | WO2005105171 | 11/2005 |
| WO | WO2005115496 | 12/2005 |
| WO | WO2006014604 | 2/2006 |
| WO | WO2006014607 | 2/2006 |
| WO | WO2006020274 | 2/2006 |
| WO | WO2006020644 | 2/2006 |
| WO | WO2006026587 | 3/2006 |
| WO | WO2006029012 | 3/2006 |
| WO | WO2006042260 | 4/2006 |
| WO | WO2006044308 | 4/2006 |
| WO | WO2006083628 | 8/2006 |
| WO | WO2006102359 | 9/2006 |
| WO | WO2006107359 | 10/2006 |
| WO | WO2006108420 | 10/2006 |
| WO | WO2006116014 | 11/2006 |
| WO | WO2006128016 | 11/2006 |
| WO | WO2006133118 | 12/2006 |
| WO | WO2007008729 | 1/2007 |
| WO | WO2007024500 | 3/2007 |
| WO | WO2007030302 | 3/2007 |
| WO | WO2007030669 | 3/2007 |
| WO | WO2007047473 | 4/2007 |
| WO | WO2007047662 | 4/2007 |
| WO | WO2007120323 | 10/2007 |
| WO | WO2007120897 | 10/2007 |
| WO | WO2007127488 | 11/2007 |
| WO | WO2008070996 | 6/2008 |
| WO | WO2008087488 | 7/2008 |
| WO | WO 2008/124310 | 10/2008 |
| WO | WO2009005933 | 1/2009 |
| WO | WO 2010/027998 | 3/2010 |

OTHER PUBLICATIONS

U.S. Appl. No. 12/238,627, filed Sep. 26, 2008, Ehrenreich et al.
Kesting, Robert E., "Phase Inversion Membranes," in Synthetic Polymeric Membranes, 2nd Ed., Chapter 7, pp. 237-286, 1985.

Tepe et al., "Local Delivery of Paclitaxel to Inhibit Restenosis During Angioplasty of the Leg," N. Engl. J. Med, 358;7, pp. 689-699, Feb. 14, 2008.
Werk et al., "Inhibition of Restenosis in Femoropopliteal Arteries Paclitaxel-Coated Versus Uncoated Balloon: Femoral Paclitaxel Randomized Pilot Trial," Circulation. 2008;118:1358-1365, Sep. 8, 2008.
U.S. Appl. No. 12/238,026, filed Sep. 25, 2008, Ehrenreich et al.
Non-Final Office Action mailed on Dec. 28, 2009 for U.S. Appl. No. 12/237,998.
Response and Amendment to Non-Final Rejection filed on Mar. 29, 2010 for U.S. Appl. No. 12/237,998.
Final Rejection mailed on Jun. 21, 2010 for U.S. Appl. No. 12/237,998.
Non-Final Rejection mailed on Feb. 8, 2010 for U.S. Appl. No. 12/238,026.
Response and Amendment to Non-Final Rejection filed on May 10, 2010 for U.S. Appl. No. 12/238,026.
U.S. Appl. No. 13/069,020, filed Mar. 22, 2011.
Response and Amendment to Final Rejection filed Aug. 23, 2010 for U.S. Appl. No. 12/237,998.
Advisory Action mailed Sep. 7, 2010 for U.S. Appl. No. 12/237,998.
Request for Continued Examination (RCE) filed Sep. 21, 2010 for U.S. Appl. No. 12/237,998.
Rejection mailed on Jul. 23, 2010 for U.S. Appl. No. 12/238,026.
Response to Final Rejection filed Sep. 23, 2010 for U.S. Appl. No. 12/238,026.
U.S. Appl. No. 12/237,998, Apr. 20, 2011 Non-Final Office Action.
U.S. Appl. No. 12/238,026, Jun. 29, 2011 Notice of Allowance.
International Search Report and Written Opinion for PCT/US2011/029327, dated Jun. 21, 2011.

* cited by examiner

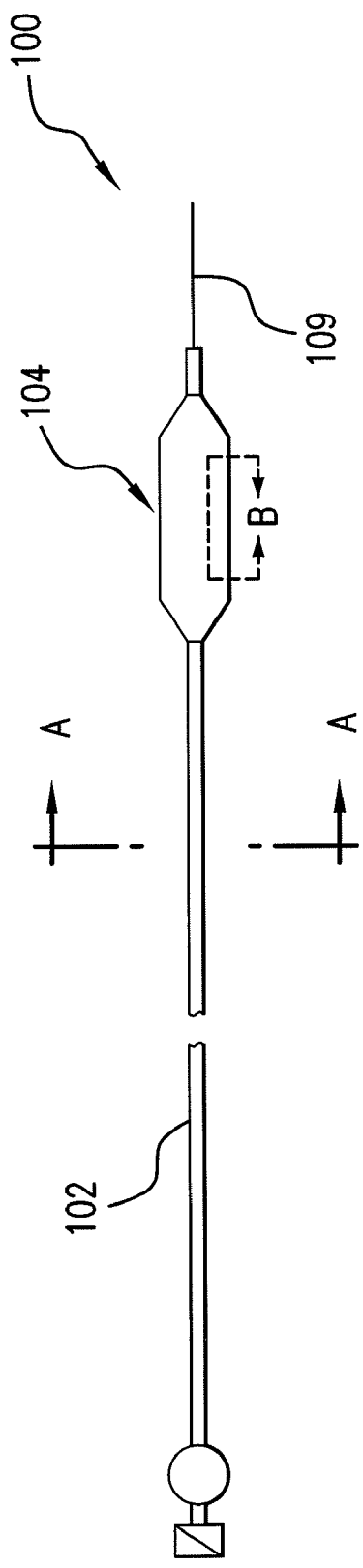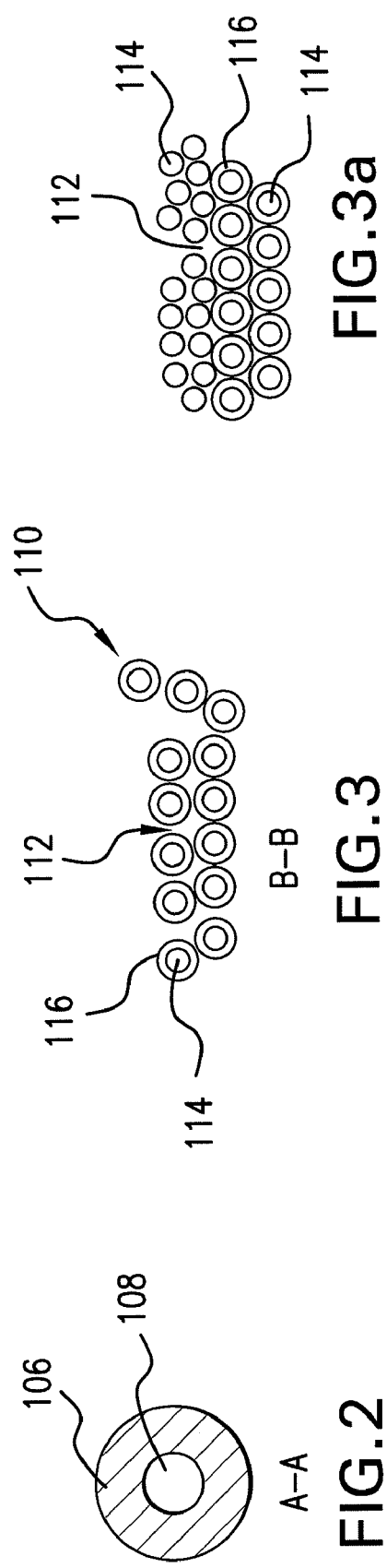

Macroscale image of electrospun
PLLA foam conduit (4.0 mm I.D.).

Surface morphology of electrospun PLLA
foam conduit by SEM (scale bar = 10 μm).

EXPANDABLE MEMBER FORMED OF A FIBROUS MATRIX FOR INTRALUMINAL DRUG DELIVERY

BACKGROUND OF THE INVENTION

1. Field of the Invention

The present invention generally relates to an intraluminal catheter device for use in angioplasty and delivery of a therapeutic agent. Particularly, the present invention is directed to a catheter having an expandable member formed of a matrix of fiber elements and suitable for insertion into the vascular system for delivering a therapeutic agent.

2. Description of Related Art

The systemic administration of therapeutic agents, such as by transoral or intravenous means, treats the body as a whole even though the disease to be treated may be localized. In some cases, systemic administration may not be desirable because the therapeutic agents may have unwanted effects on parts of the body which are not to be treated, or because treatment of the diseased part of the body requires a high concentration of a therapeutic agent that may not be achievable by systemic administration.

It is therefore often desirable to administer therapeutic agents at localized sites within the body. Common examples include cases of localized vascular disease (e.g., heart disease) or diseased body lumens. Among the treatments becoming available for local treatment of vascular disease, are drug-eluting balloons. This type of medical device is typically a percutaneous transluminal coronary angioplasty (PTCA) balloon catheter that carries a therapeutic agent on the surface of the balloon for delivery to the vessel wall. The method generally includes the steps of adding a therapeutic agent to the balloon surface using any of a number of manufacturing processes, such as dip coating, spray coating, painting or pipetting onto the balloon, electron ion deposition, or plasma gamma discharge deposition, inserting the catheter into a blood vessel to a desired location, and expanding the catheter balloon against the surrounding tissue to allow the release of the drug.

In these cases, the therapeutic agent disposed on the balloon surface is exposed to the surrounding environment. As a result, it may contact the vascular surface as the device is tracked through the vessel to the treatment site, resulting in loss of the therapeutic agent and a reduced dose of the therapeutic agent to the target site. A further drawback is the premature diffusion of the drug during delivery into the body.

In view of the potential drawbacks to conventional drug delivery techniques, there exists a need for a device and method for the controlled, localized delivery of therapeutic agents to target locations or lesions within a mammalian body, while preventing the premature release or removal of the therapeutic agent during delivery.

SUMMARY OF THE INVENTION

The purpose and advantages of the present invention will be set forth in and apparent from the description that follows, as well as will be learned by practice of the invention. Additional advantages of the invention will be realized and attained by the methods and systems particularly pointed out in the written description and claims hereof, as well as from the appended drawings.

To achieve these and other advantages and in accordance with the purpose of the invention, as embodied and broadly described, the invention includes a catheter device provided for intraluminal delivery of at least one therapeutic agent within a lumen or by contacting the vessel wall. Particularly, the catheter device includes an elongated catheter shaft having a proximal end portion and distal end portion and an inflation lumen disposed between the proximal end portion and the distal end portion. The catheter device includes an expandable member which is formed of a matrix of fiber elements and is disposed proximate to the distal end of the catheter shaft. The expandable member is formed of a matrix of fiber elements which is configured to define an inner chamber for the expandable member. The fibers are formed from polymers, such as for example, but not limited to, polyamides, polyurethanes, silicone modified polyurethanes, fluoropolymers, polyolefins, polyimides, polyimines, (methyl) acrylic polymers, polyesters, polyglycolide, polyglycolide (PGA), poly(L-lactide) (PLLA), poly(D,L-lactide) (PDLLA), poly(L-lactide-co-glycolide) (PLGA), poly(D,L-lactide-co-glycolide) (PDLGA), poly($\epsilon$-caprolactone) (PCL), polydioxanone, poly(ethylene glycol) (PEG), poly (vinyl alcohol), and co-polymers thereof.

In accordance with a preferred embodiment of the invention, the matrix of fiber elements are formed by an electrospinning process. Electrospinning is a method based on the ability of an electric field to overcome the surface tension of a polymer or biomacromolecule solution (or melt), and form a conical shape called the Taylor cone. Depending on the solution and process parameters such as polymer concentration, molecular weight, nozzle diameter, charge magnitude, spinning distance, and solution feed rate, continuous fibers can be produced that can have diameters ranging from a few hundred nanometers to several microns.

In accordance with the invention, a therapeutic agent is dispersed on the expandable member. In one embodiment, the therapeutic agent is coated on the individual fiber elements that form the expandable member. Preferably, the therapeutic coating completely surrounds the fiber. Alternatively, the therapeutic agent can partially coat the fiber.

In accordance with yet another embodiment, the expandable member defines an outer surface, and the therapeutic agent is coated on the outer surface of the expandable member. Alternatively, the therapeutic agent can coat both the individual fibers and also the outer expandable member surface. The therapeutic agents include for example, anti-proliferative, anti-inflammatory, antineoplastic, antiplatelet, anticoagulant, anti-fibrin, antithrombotic, antimitotic, antibiotic, antiallergic and antioxidant compounds.

It is contemplated that in an alternative embodiment the expandable member may also be used to deliver angiogenic factors. Growth factors, such as isoforms of vasoendothelial growth factor (VEGF), fibroblast growth factor (FGF, e.g., beta-FGF), Del 1, hypoxia inducing factor (HIF 1-alpha), monocyte chemoattractant protein (MCP-1), nicotine, platelet derived growth factor (PDGF), insulin-like growth factor (HGF), estrogens, folliostatin, proliferin, prostaglandin E1 and E2, tumor necrosis factor (TNF-alpha), interleukin 8 (Il-8), hematopoietic growth factors, erythropoietin, granulocyte-colony stimulating factors (G-CSF) and platelet-derived endothelial growth factor (PD-ECGF). In some embodiments, angiogenic factors include, but are not limited to, peptides, such as PR39, PR11, and angiogenin, small molecules, such as PHD inhibitors, or other agents, such as eNOS enhancers.

In accordance with one embodiment of the invention, a protective substance can coat the therapeutic agent. In one embodiment, the protective coating is a second coating on the fiber elements, completely or partially surrounding the first coating of a therapeutic agent. Alternatively, the protective substance coats at least one portion of the therapeutic coating on the outer surface of the expandable member. The protective coating prevents the therapeutic agent from eluting prematurely from the expandable member surface as the device is delivered through the anatomy to the target site. Suitable substances which can be effective as a protective coating include, but are not limited to glucose, hydrophilic coatings, biodegradable materials, substances which are dissolvable in blood or aqueous mediums, or other substances which will crack under expansion and will therefore allow the therapeutic agent to contact the vessel wall.

In accordance with the invention, the intraluminal catheter is used to deliver a therapeutic agent to a desired treatment site. The intraluminal catheter device has an elongated catheter shaft having a proximal end portion and a distal end portion and an inflation lumen disposed between the proximal end portion and the distal end portion. An expandable member that has a therapeutic agent dispersed thereon is disposed proximate to the distal end portion of the catheter. The expandable member is formed of a matrix of fiber elements and the therapeutic agent is coated on the fiber elements. Additionally or alternatively, the outer surface of the expandable member can be coated with a therapeutic agent. The catheter is advanced to a desired treatment site and fluid is introduced into the inflation lumen to expand the expandable member and release the therapeutic agent into the vessel wall.

It is to be understood that both the foregoing general description and the following detailed description are exemplary and are intended to provide further explanation of the invention claimed.

The accompanying drawings, which are incorporated in and constitute part of this specification, are included to illustrate and provide a further understanding of the product and method of the invention. Together with the description, the drawings serve to explain the principles of the invention.

BRIEF DESCRIPTION OF THE DRAWINGS

FIG. 1 is a plan view of a catheter having an expandable member constructed of a plurality of fibers in accordance with the invention;

FIG. 2 is a cross-sectional view taken along lines A-A in FIG. 1 in accordance with one embodiment of the present invention;

FIG. 3 is a cross-sectional view taken along lines B-B in FIG. 1 in accordance with one embodiment of the present invention;

FIG. 3a is a cross-sectional view taken along lines B-B in FIG. 1 in accordance with another embodiment of the present invention;

FIGS. 11a-11d are time-course images of an electrospun expandable member undergoing ethylene oxide sterilization, resulting in a fluid tight member.

DETAILED DESCRIPTION OF THE PREFERRED EMBODIMENT

Figure 4:
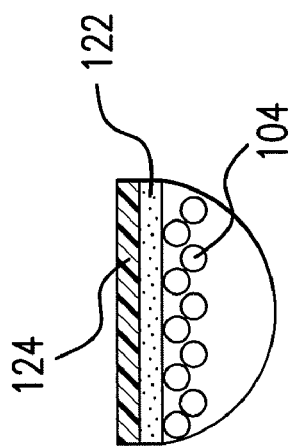
FIG. 4 is a cross-section view of the fiber element of the expandable member in accordance with an alternative embodiment of the present invention.

Reference will now be made in detail to the present preferred embodiments of the invention. The method and corresponding steps of the invention will be described in conjunction with the detailed description of the intravascular catheter device.

In accordance with the present invention, an intraluminal catheter device is provided for delivery of at least one therapeutic agent within a lumen by contacting the vessel wall. Particularly, the catheter device includes an elongated catheter shaft having a proximal end portion and a distal end portion and an expandable member located proximate to the distal end portion of the catheter shaft, the expandable member constructed of a matrix of fiber elements. In accordance with one embodiment of the invention, the expandable member is fabricated by electrospinning of the fibers into a matrix configuration. Alternatively, the expandable member can be fabricated by melt-blowing or spunbonding processes to create the fibrous matrix.

The expandable member formed from a matrix of fibers contains a therapeutic agent incorporated therein. The catheter is configured for delivery through an anatomy and to a target treatment site. In accordance with one embodiment of the invention, once positioned near the target treatment site, the expandable member is inflated and the therapeutic agent is delivered to the diseased site and provides a beneficial effect. In one embodiment, the expandable member contacts the vasculature wall upon expansion and the therapeutic agent is delivered to the vessel wall.

An exemplary embodiment of the intravascular catheter device in accordance with the present invention is shown schematically in FIGS. 1 and 2, for purposes of illustration only and not limitation. As shown in FIGS. 1 and 2, the intraluminal medical device 100 generally includes an elongated catheter shaft 102 having a proximal end and having a distal end and an expandable member 104 located proximate to the distal end of the catheter shaft. An inflation lumen 106 can be disposed between the proximal end portion and the distal end portion of the catheter shaft 102. The expandable member 104 is placed in fluid communication with the inflation lumen. The inflation lumen can supply fluid under pressure, and establish negative pressure, to the expandable member. The expandable member 104 can thus be inflated and deflated. The elongated catheter is sized and configured for delivery through a tortuous anatomy, and can further include a guidewire lumen 108 that permits it to be delivered over a guidewire 109. The guidewire lumen can have an over-the-wire (OTW) or rapid-exchange (RX) construction, as is well known in the art. Alternatively, the catheter body can include a fixed guidewire to permit the catheter to be delivered to a vessel location without the use of a separate guidewire.

The expandable member is formed of a matrix of fiber elements 110. The matrix configuration allows for a highly accessible surface area of the expandable member. The diameter of the fibers range can from nano to micro in size; preferably from 20 nanometers to 20 micrometers, more preferably from 200 nanometers to 200 micrometers. Accordingly, a vast majority of fibers are required to form an expandable structure configured to be disposed at distal portion of catheter shaft. Further, the fiber elements are configured to achieve a desired thickness of the expandable member. In accordance with a preferred embodiment of the invention, the expandable member thickness ranges from 1 micrometer to 500 micrometers, and preferably 5 micrometers to 50 micrometers, based on the fiber size and number of layers deposited.

In accordance with the invention and as illustrated in FIG. 3, as a result of the overlapping matrix configuration of the fiber elements, small gaps 112 are present between the adjacent fibers of the matrix. The diameter of each fiber as well as the configuration of overlapping fibers will affect the gap size of the matrix since it essentially dictates the opening that exists between the fiber elements of the matrix. Processing parameters such as nozzle position and solution composition, among others, can also impact the gap size. The matrix can include gaps of similar or significantly different sizes throughout. In accordance with the invention, the gaps 112 are sized and configured to allow the expandable member to expand from a first profile to a second profile. In this regard, the fiber matrix is configured to allow the expandable member to easily expand and contact the vessel wall such that the therapeutic agent will be delivered to the vessel wall for treatment of vascular disease. In accordance with one embodiment, the fibrous matrix is configured such that the expandable member is essentially fluid-tight and can maintain an expanded profile for an extended period of time. Alternatively, the fiber matrix is configured such that the expandable member is not necessarily fluid-tight, however the configuration of the fibers allows the expandable member to expand from a first profile to second profile and contact the vessel wall such that the therapeutic agent can be effectively delivered within a lumen by contacting the vessel wall.

For purpose of illustration and not limitation as illustrated in FIG. 3, the polymeric fiber 110 includes a core 114 that is composed of one or more polymeric materials. The polymeric material of the fiber include, but are not limited to, polyamides, polyurethanes, fluoropolymers, polyolefins, polyimides, polyimines, (methyl)acrylic polymers, polyesters, polyglycolide (PGA), poly(L-lactide) (PLLA), poly(D,L-lactide) (PDLLA), poly(L-lactide-co-glycolide) (PLGA), poly(D,L-lactide-co-glycolide) (PDLGA), poly(ϵ-caprolactone) (PCL), polydioxanone, poly(ethylene glycol) (PEG), poly(vinyl alcohol), and suitable copolymers thereof, poly (ester amides) (PEA), and biodegradable elastomers such as biodegradable poly(ester urethanes) (PEU), polyhydroxyalkanoates such as poly(4-hydroxybutyrate) or poly(3-hydroxybutyrate), poly(1,3-trimethylene carbonate). Alternatively, the core 114 can be a combination of one or more polymeric materials.

In accordance with one embodiment of the invention, the plurality of fibers include at least one coating completely or partially surrounding the polymeric core. For example, and as shown in FIG. 3, for the purposes of illustration, the plurality of fibers include a coating 116 having at least one therapeutic agent. Preferably, the therapeutic agent coating completely surrounds the polymeric core in a co-axial configuration. In this regard, the expandable member is provided with a therapeutic agent for delivery within a vasculature to a targeted area. The matrix and structure provided by the plurality of fibers protects the therapeutic agent from eluting from the surface of the expandable member during the time required to place the device within the vessel lumen and reach the targeted area. Once the target lesion, is reached, the member 104 is expanded and the therapeutic agent 116 is brought into contact with the vessel wall.

In accordance with an another embodiment of the invention, and as shown in FIG. 3a, for illustration, a second layer of electrospun fibers without any therapeutic agent can be spun over the layer of fibers with the therapeutic agent to provide additional protection and to inhibit therapeutic agent from prematurely eluting from the surface of the expandable member. Alternatively, uncoated fibers can be disposed toward the inner surface of the expandable member and therapeutic agent coated fibers toward the outside, to allow for a thicker wall with reduced use of drug. Yet another embodiment includes a matrix formed with both coated and uncoated fibers intermixed with each other.

In accordance with an alternative embodiment of the invention, and as illustrated in FIG. 4, the fiber can have a second coating 120. The second coating can partially or completely surround the first coating 116. In a preferred embodiment of the invention, the second coating 120 comprises a material that is generally impervious to the elution of the therapeutic agent incorporated in the first coating. The second coating 120 acts as a protective coating for the therapeutic agent and, thereby, prevents premature elution of the therapeutic agent prior to proper placement within the vessel lumen at a treatment site. Further, this protective layer prevents physical damage to the therapeutic layer during insertion. In accordance with a preferred embodiment of the invention, the protective coating 120 comprises a protective substance that is dissolvable, biodegradable or disintegrable upon expansion or inflation of the expandable member. For purpose of illustration and not limitation, the protective substance includes glucose, hydrophilic substances, biodegradable substances, contrast mediums, mediums which are dissolvable in blood or aqueous mediums, or other mediums which will crack under expansion and will therefore allow the therapeutic agent to contact the vessel wall. Suitable binders and solvents also can be used to enhance performance of this layer.

Alternatively, the second coating can be a second layer of a second therapeutic agent. The therapeutic agent in the second coating can be different or alternatively, identical to the first therapeutic agent in the first coating. This configuration of therapeutic agents in two separate coatings can allow for different release rates of the therapeutic agents. The second coating also can be a primer material that adheres to the first layer material and allows a third layer coating to be added having a second therapeutic agent.

Figure 5:
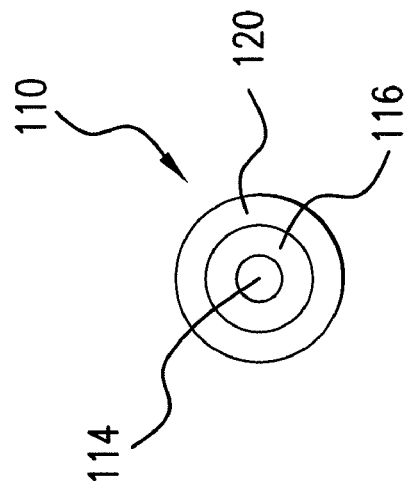
FIG. 5 is a cross-sectional view of the expandable member in accordance with another embodiment of the present invention.

In accordance with a further embodiment of the invention, as illustrated in FIG. 5, the therapeutic agent 122 can be directly applied to the surface of the expandable member 104. For example and not limitation, the therapeutic coating 122 can be applied by techniques including powder coatings, spray coating, dip coating, pad printing, transfer by rolling, electrografting, and electrostatic coating, as understood in the art. The therapeutic agent can be coated over a portion or the entirety of the expandable member 104. In accordance with one aspect of the invention, the therapeutic agent 122 is only present on the surface of the expandable member 104 formed of a matrix of fiber elements. Alternatively, the therapeutic agent can be present as both a coating 116 on the fiber elements 110 of the expandable member and as a separate coating 122 on the outer surface of the expandable member 104.

As embodied herein and depicted in FIG. 5, and further in accordance with another aspect of the invention, the protective material 124 can be coated over a portion or the entirety of the inflatable structure 104 using similar methods. As discussed above, the protective material acts as a protective coating for the therapeutic agent and, thereby, prevents premature elution of the drug or therapeutic substance prior to proper placement within the vessel lumen at a treatment site. The dissolvable coating protects the therapeutic agent as the device is delivered through the anatomy to the target site. In accordance with one aspect of the invention, and as depicted in FIG. 5, the protective substance 124 coats the layer of therapeutic agent 122 which has been coated, such as, for example by dip or spray coating techniques, on the outer surface of expandable member 104. Alternatively, the protective substance can be coated on the outer surface of the expandable member, where the expandable member is formed of a matrix of fiber elements having a therapeutic agent coated on the fiber elements.

In another embodiment of the invention, the therapeutic agent can be dispersed and encapsulated within each fiber, such that each fiber strand consists of a single layer, the layer including polymer and a therapeutic agent. In this embodiment, the polymer and therapeutic agent are not in a co-axial arrangement, or a layered arrangement, instead the fiber strand includes a polymer with a therapeutic agent dispersed throughout.

In accordance with yet another embodiment of the invention, the gaps 112 of the expandable member can be filled with a therapeutic agent. Alternatively, the therapeutic agent may be contained in microparticles, such as microspheres and microcapsules, which are incorporated in the gaps 112 of the expandable member.

The therapeutic agent can be delivered from the expandable member by introducing inflation fluid through the catheter body and into the expandable member. Once pressure builds within the expandable member it inflates or expands. The expandable member is configured to provided a radial force against the vessel wall during expansion. In one embodiment, the expansion allows the expandable member to contact the vessel wall and the therapeutic agent to be delivered into the vessel wall at the target treatment site. This radial force ensures that the expandable member can expand safely, without causing harm to the vessel wall. Additionally, reducing the stress in the vessel wall can also contribute to a higher rate of uptake of therapeutic agent within the vessel wall as well as improved retention of the therapeutic agent after the catheter has been delivered and removed. The expansion force can be achieved by selecting the appropriate property of the matrix of fiber elements, such as, for example, modulus, gap size, porosity, fiber cross-sectional area or fiber packing density. In an alternative embodiment, the expandable member is inflated and the therapeutic agent is allowed to disperse into the area surrounding the target treatment site.

For example and not limitation, at least one therapeutic agent can include anti-proliferative, anti-inflammatory, antineoplastic, antiplatelet, anti-coagulant, anti-fibrin, anti-thrombotic, antimitotic, antibiotic, antiallergic and antioxidant compounds. Thus, the therapeutic agent can be, again without limitation, a synthetic inorganic or organic compound, a protein, a peptide, a polysaccharides and other sugars, a lipid, DNA and RNA nucleic acid sequences, an antisense oligonucleotide, an antibodies, a receptor ligands, an enzyme, an adhesion peptide, a blood clot agent including streptokinase and tissue plasminogen activator, an antigen, a hormone, a growth factor, a ribozyme, a retroviral vector, an anti-proliferative agent including rapamycin (sirolimus), 40-O-(2-hydroxyethyl)rapamycin (everolimus), 40-O-(3-hydroxypropyl)rapamycin, 40-O-(2-hydroxyethyoxy)ethylrapamycin, 40-O-tetrazolylrapamycin (zotarolimus, ABT-578), paclitaxel, docetaxel, methotrexate, azathioprine, vincristine, vinblastine, fluorouracil, doxorubicin hydrochloride, and mitomycin, an antiplatelet compound, an anticoagulant, an antifibrin, an antithrombins including sodium heparin, a low molecular weight heparin, a heparinoid, hirudin, argatroban, forskolin, vapiprost, prostacyclin, a prostacyclin analogue, dextran, D-phe-pro-arg-chloromethylketone (synthetic antithrombin), dipyridamole, glycoprotein IIb/IIIa platelet membrane receptor antagonist antibody, recombinant hirudin, a thrombin inhibitor including Angiomax ä, a calcium channel blocker including nifedipine, colchicine, a fibroblast growth factor (FGF) antagonist, fish oil (omega 3-fatty acid), a histamine antagonist, lovastatin, a monoclonal antibody, nitroprusside, a phosphodiesterase inhibitor, a prostaglandin inhibitor, suramin, a serotonin blocker, a steroid, a thioprotease inhibitor, triazolopyrimidine, a nitric oxide or nitric oxide donor, a super oxide dismutase, a super oxide dismutase mimetic, estradiol, an anticancer agent, a dietary supplement including vitamins, an anti-inflammatory agent including aspirin, tacrolimus, dexamethasone and clobetasol, a cytostatic substance including angiopeptin, an angiotensin converting enzyme inhibitor including captopril, cilazapril or lisinopril, an antiallergic agent including permirolast potassium, alpha-interferon, bioactive RGD, and genetically engineered epithelial cells. Other therapeutic agents which are currently available or that may be developed in the future for use with intraluminal catheter devices may likewise be used and all are within the scope of this invention.

For example and not limitation, the therapeutic agents effective in preventing restenosis, including those classified into the categories of anti-proliferative agents, anti-platelet agents, anti-inflammatory agents, anti-thrombotic agents, and thrombolytic agents can be further sub-divided. For example, anti-proliferative agents can be anti-mitotic. Anti-mitotic agents inhibit or affect cell division, whereby processes normally involved in cell division do not take place. One sub-class of anti-mitotic agents includes vinca alkaloids. Representative examples of vinca alkaloids include, but are not limited to, vincristine, paclitaxel, etoposide, nocodazole, indirubin, and anthracycline derivatives, including, for example, daunorubicin, daunomycin, and plicamycin. Other sub-classes of anti-mitotic agents include anti-mitotic alkylating agents, including, for example, tauromustine, bofumustine, and fotemustine, and anti-mitotic metabolites, including, for example, methotrexate, fluorouracil, 5-bromodeoxyuridine, 6-azacytidine, and cytarabine. Anti-mitotic alkylating agents affect cell division by covalently modifying DNA, RNA, or proteins, thereby inhibiting DNA replication, RNA transcription, RNA translation, protein synthesis, or combinations of the foregoing.

An example of an anti-mitotic agent includes, but is not limited to, paclitaxel. As used herein, paclitaxel includes the alkaloid itself and naturally occurring forms and derivatives thereof, as well as synthetic and semi-synthetic forms thereof.

Anti-platelet agents are therapeutic entities that act by (1) inhibiting adhesion of platelets to a surface, typically a thrombogenic surface, (2) inhibiting aggregation of platelets, (3) inhibiting activation of platelets, or (4) combinations of the foregoing. Activation of platelets is a process whereby platelets are converted from a quiescent, resting state to one in which platelets undergo a number of morphologic changes induced by contact with a thrombogenic surface. These changes include changes in the shape of the platelets, accompanied by the formation of pseudopods, binding to membrane receptors, and secretion of small molecules and proteins, including, for example, ADP and platelet factor 4. Anti-platelet agents that act as inhibitors of adhesion of platelets include, but are not limited to, eptifibatide, tirofiban, RGD (Arg-Gly-Asp)-based peptides that inhibit binding to gpIbIIIa or avb3, antibodies that block binding to gpIIaIIIb or avb3, anti-P-selectin antibodies, anti-E-selectin antibodies, compounds that block P-selectin or E-selectin binding to their respective ligands, saratin, and anti-von Willebrand factor antibodies. Agents that inhibit ADP-mediated platelet aggregation include, but are not limited to, disagregin and cilostazol.

As discussed above, at least one therapeutic agent can be an anti-inflammatory agent. Non-limiting examples of anti-inflammatory agents include prednisone, dexamethasone, hydrocortisone, estradiol, triamcinolone, mometasone, fluticasone, clobetasol, and non-steroidal anti-inflammatories, including, for example, acetaminophen, ibuprofen, naproxen, adalimumab and sulindac. The arachidonate metabolite prostacyclin or prostacyclin analogs is an example of a vasoactive antiproliferative. Other examples of these agents include those that block cytokine activity or inhibit binding of cytokines or chemokines to the cognate receptors to inhibit pro-inflammatory signals transduced by the cytokines or the chemokines. Representative examples of these agents include, but are not limited to, anti-IL1, anti-IL2, anti-IL3, anti-IL4, anti-IL8, anti-IL15, anti-IL18, anti-MCP1, anti-CCR2, anti-GM-CSF, and anti-TNF antibodies.

Anti-thrombotic agents include chemical and biological entities that can intervene at any stage in the coagulation pathway. Examples of specific entities include, but are not limited to, small molecules that inhibit the activity of factor Xa. In addition, heparinoid-type agents that can inhibit both FXa and thrombin, either directly or indirectly, including, for example, heparin, heparin sulfate, low molecular weight heparins, including, for example, the compound having the trademark Clivarin®, and synthetic oligosaccharides, including, for example, the compound having the trademark Arixtra®. Also included are direct thrombin inhibitors, including, for example, melagatran, ximelagatran, argatroban, inogatran, and peptidomimetics of binding site of the Phe-Pro-Arg fibrinogen substrate for thrombin. Another class of anti-thrombotic agents that can be delivered are factor VII/VIIa inhibitors, including, for example, anti-factor VII/VIIa antibodies, rNAPc2, and tissue factor pathway inhibitor (TFPI).

Thrombolytic agents, which can be defined as agents that help degrade thrombi (clots), can also be used as adjunctive agents, because the action of lysing a clot helps to disperse platelets trapped within the fibrin matrix of a thrombus. Representative examples of thrombolytic agents include, but are not limited to, urokinase or recombinant urokinase, pro-urokinase or recombinant pro-urokinase, tissue plasminogen activator or its recombinant form, and streptokinase.

Other therapeutic agents include cytotoxic drugs, including, for example, apoptosis inducers, including TGF, and topoisomerase inhibitors, including, 10-hydroxycamptothecin, irinotecan, and doxorubicin. Other therapeutic agents include drugs that inhibit cell de-differentiation and cytostatic drugs. The at least one therapeutic agent can also include anti-lipaedemic agents, including fenofibrate, matrix metalloproteinase inhibitors, including, for example, batimistat, antagonists of the endothelin-A receptor, including, for example, darusentan, and antagonists of the avb3 integrin receptor.

Figure 6A:
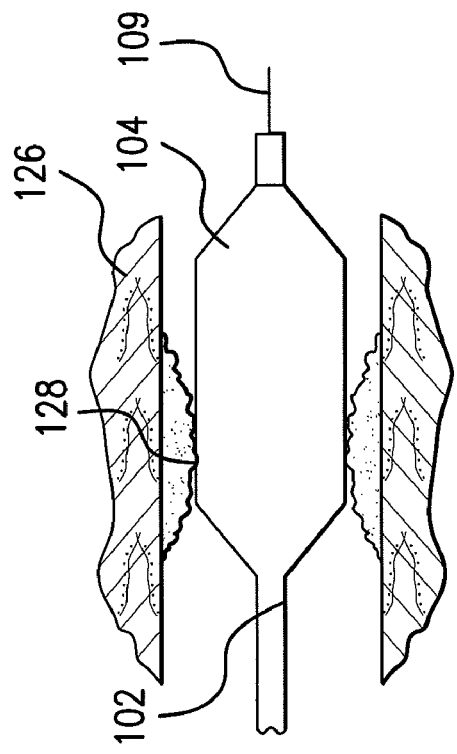
FIGS. 6a and 6b are planar views of a method of use of a catheter having an expandable member constructed of a plurality of fibers.
Figure 6B:
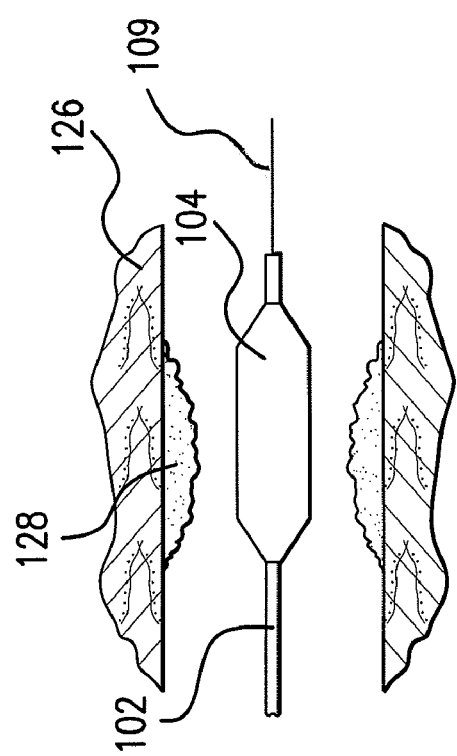

A method of use is therefore provided in accordance with this invention, the method having the following steps. As illustrated in FIG. 6a, the catheter 100 is advanced over a guidewire 109 through the vasculature 126 until the expandable member 104 is positioned adjacent to the target disease or desired treatment site 128. As illustrated in FIG. 6b, inflation fluid is introduced through the catheter body and into the expandable member to expand or inflate the expandable member 104. The therapeutic agent can be delivered to the vasculature by several techniques. One method of delivering the therapeutic agent includes diffusion of the therapeutic agent from the fiber to the vessel wall when the expandable member is expanded against the vessel wall. Particularly, a preferred method includes using a suitable solvent, such as saline, water, contrast, water/ethanol mixture, or water/ DMSO mixture, to enhance the release of the drug from the fiber upon inflation of the expandable member. Another method of delivery includes a burst release technique, wherein the fibers are expanded or stretched as the expandable member is expanded from a first profile to a second profile and the therapeutic agent is thereby released from the fiber matrix and into the vessel wall and surrounding area. It will also be appreciated that a method of delivery may incorporate both a burst release and a diffusion release technique, in accordance with this invention.

Any suitable process for forming an expandable member from a matrix of fiber elements can be used in accordance with the present invention. As discussed above, the expandable member is a shaped structure formed from many fibers that exist in a matrix configuration. As a result of the matrix-like configuration which is tightly woven and overlapped, the expandable member can be expanded with a pressurizing or inflation fluid. Suitable processes for creating the fibrous matrix which is formed into an expandable member include, for example, electrospinning, melt-blowing or spunbonding.

In accordance with a preferred embodiment of the invention, the expandable member is formed by an electrospinning process. Due to the wide variety of materials that can be used for the electrospinning process, the expandable member can be formed from a relatively soft material, which will improve deliverability of the device, and prevent damage to the anatomy during delivery. Additionally, the electrospinning process allows for the fibers to be formed with one or more coatings. In accordance with one embodiment, and as discussed above, the fibers include a base material that supplies structure to the expandable member, and a first coating formed from one or more therapeutic agents. It is also possible to provide a second coating placed over the therapeutic agent on the electrospun fibers. The second coating can be a protective coating is dissolvable or disintegrable upon inflation of the expandable member.

Figure 7:
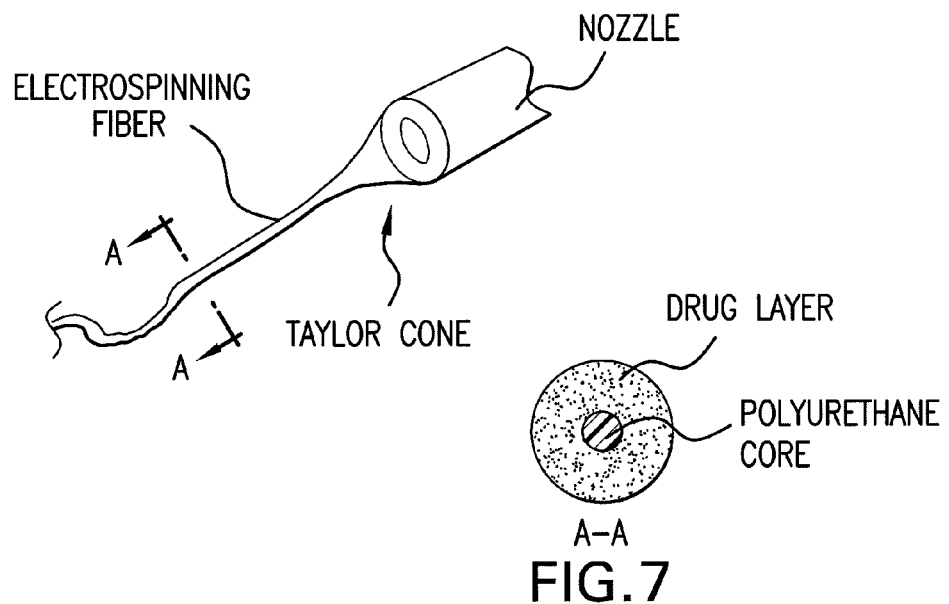
FIGS. 7 and 8 are schematic drawings of an exemplary electrospinning process used to form the expandable member of the present invention.
Figure 8:
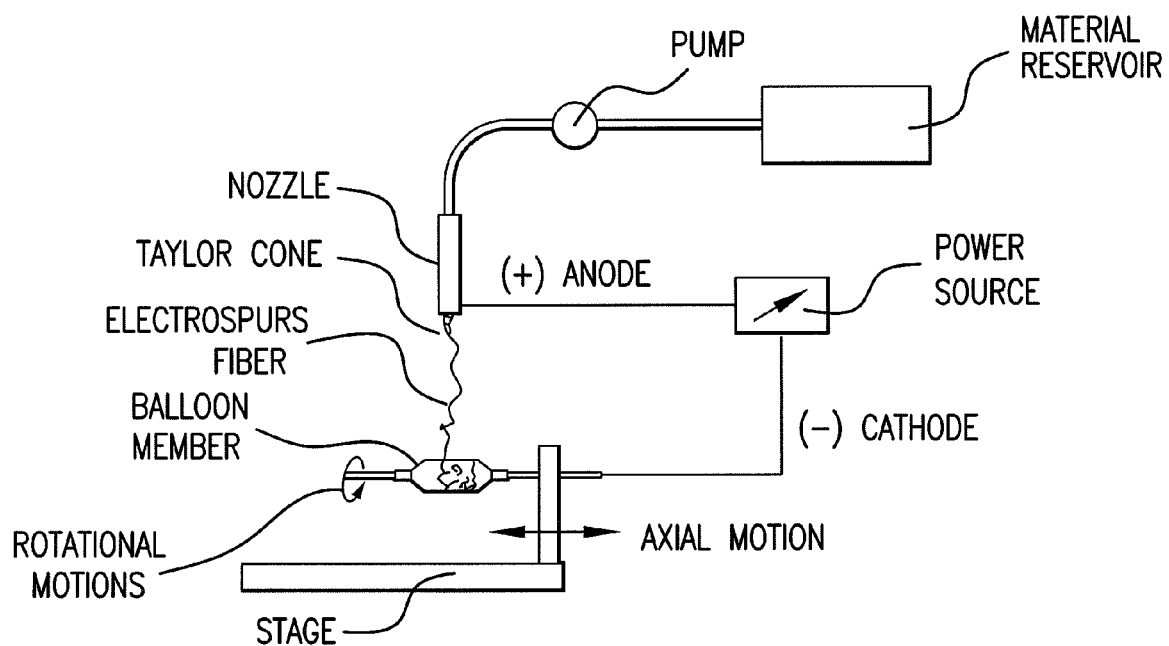

In accordance with a preferred embodiment of the present invention, and as illustrated in FIGS. 7 and 8, for purpose of illustration and not limitation, a method of electrospinning an inflatable member is provided. The process in forming an expandable member, such as a balloon, includes providing a forming mandrel with a profile that is approximately the same as the desired expandable member profile. Material fibers are then electrospun onto the mandrel surface. For example, and not limitation, the electrospun fibers are formed from polyurethane dissolved in a solvent such as acetone, tetrahydrofuran, N,N-dimethylformamide, chloroform, trifluoroethanol, hexafluoroisopropanol, or blends thereof. During the electrospinning process, the solvent begins to evaporate. When the electrospinning fibers reach the mandrel surface, the remainder of the solvent evaporates leaving the electrospun fibers. As the electrospinning layers are added, additional crossing of the electrospinning fibers will result in a dense matrix of material having radial channels or gaps passing therethrough. The size and location of these channels and gaps can be controlled through various process parameters, such as solution composition, nozzle position, and other parameters known in the art.

For example, U.S. Pat. Nos. 6,382,526 and 6,520,425 incorporated herein by reference in their entirety, are directed to a process and apparatus for the production of nanofibers. An electrospinning fixture is provided that includes a working stage for holding the mandrel that the electrospun material matrix will be formed on. This stage should include rotational and axial movement capabilities and the motion of the stage is to be controlled by a motor synchronized with a motor controller. The stage includes a holding fixture such as a chuck that accepts the balloon member and transmits motion thereto. The holding fixture is also connected to the negative lead of a power source, making it the cathode of the electrolytic process. The positive lead of a power source is connected to the ejection nozzle, making the nozzle the anode of the electrolytic process.

Typically, electrospinning processes require high voltage but relatively low current. In one embodiment of this invention, the power source is capable of delivering 0 to 60 kilovolts of electrical potential, but generally operates in the range of 10 to 20 kilovolts during the electrospinning process. The current that is provided by the power source is generally in the 5 to 10 microampere range. It will be appreciated that these ranges can vary depending upon the electrospinning material and process parameters. Also, it can be preferable to utilize two power sources placed in parallel or in series, depending on the goals of the process.

The nozzle is connected to a reservoir filled with electrospinning material dissolved in a solvent, and is placed in fluid communication with the reservoir by a fluid transport lumen and a pump. The electrospinning material includes thermoplastic polymeric material discussed above in connection with the material of the expandable member. Suitable organic or aqueous based electrospinning solvents, include but are not limited to, acetone, methyl ethyl ketone, cyclohexanone, dichloromethane, chloroform, trifluoroethanol, hexafluoroisopropanol, tetrahydrofuran, N,N-dimethylformamide, ethyl acetate, isopropanol, ethanol, water or blends thereof. A particular embodiment of electrospinning material includes polyurethane dissolved in tetrahydrofuran, although this can be varied widely depending upon the requirements of the invention.

The nozzle can be located in a position that creates the desired electrospinning pattern. For example, if a random matrix pattern is desirable, the nozzle exit can be located greater than about 3 mm from the expandable member surface. If a more controlled pattern is desired, the nozzle can be located within about 3 mm from the expandable member surface. The nozzle exit inner diameter will typically be in the range of about 500 micrometer to 1.5 mm in order to achieve the desired electrospinning fiber size.

The electrospinning fiber will normally be ejected from the Taylor cone adjacent to the anode toward the cathode. The fibers will preferably have diameters in the range of about 20 nanometer to 10 micrometer. This size range will affect the gap size of the matrix since it will determine how much gap exists between overlapping fibers. The density of the fibers and the number of fiber layers will also affect the gap size. It is important to note that various changes to the electrospinning fibers can be made in accordance with this invention, which will affect the efficacy of the solution. For example, it is possible to electrospin a fiber that has two layers, a core (inner layer) and an outer coating (outer layer), by utilizing a specific capillary nozzle, as shown in FIG. 7. This construction will form an electrospinning fiber that has, for example, a polyurethane core and a therapeutic agent outer coating. Likewise, a second coating (third layer) can be simultaneously spun, which can be a protective coating dissolvable in a solvent. Alternatively, electrospun fiber can have a therapeutic agent core and a polymer outer layer or coating.

In accordance with yet another embodiment, the fibers are spun into single layer strands having a therapeutic agent dispersed throughout the polymeric fiber using a conventional nozzle. During the electrospinning process, the therapeutic agent is mixed in the same solution as the solvent and the polymer. The solution is then sprayed from a single opening nozzle to form fiber strands having a homogeneous or phase separated distribution of therapeutic agent in the polymeric fiber.

To maximize fiber bonding and minimize layer delamination within the electrospun expandable member, fabrication distance can be lowered to an appropriate value to cause fibers to lightly bond between layers due to presence of more solvent with less evaporation distance. As is well know in the art, a shorter process distance results in wetter fibers and tighter junctions.

Further process variables such as polymer solution concentration as stated previously can also affect both morphology and fiber diameter. Increasing polymer concentration and solution viscosity while holding all other variables constant generally results in larger fiber diameter. Fiber diameters can then be varied from tens of nanometers to greater than a micron based on the parameters used. Wall thickness of the nanofiber expandable member could be controlled from tens of microns up to a millimeter or greater by adjusting fabrication time from a few minutes up to an hour or more. Fabrication parameters and material composition can also be optimized for each particular catheter delivery system, to allow for the desired radial force, flexibility and recoverability.

In accordance with another embodiment, the fibrous matrix which is formed into an expandable balloon is formed from a melt-blowing or spunbonding process. The melt blowing process is well known in the art and involves extruding a fiber-forming thermoplastic polymer resin in molten form through orifices of a heated nozzle into a stream of hot gas to attenuate the molten resin as fibers which form a fiber stream, the fibers being collected on a receiver in the path of the fiber stream to form a nonwoven web. The fibrous web can then be shaped into an expandable member. A method for producing a melt-blown fibrous web is described in U.S. Pat. No. 3,978,185 to Buntin et al., which is incorporated herein by reference in its entirety. The spunbonding process, equally well know in the art, is similar to the melt-blowing process, the two major differences between the two processes being i) the temperature and volume of the air used to attenuate the filaments and ii) the location where the filament draw or attenuation force is applied. A melt-blowing process uses large amounts of high-temperature air to attenuate the filaments. The air temperature is typically equal to or slightly greater than the melt temperature of the polymer. In contrast, the spunbonding process generally uses a smaller volume of air close to ambient temperature to first quench the fibers and then to attenuate the fibers. Methods for producing spunbonded webs are disclosed in U.S. Pat. No. 3,338,992 and U.S. Pat. No. 3,341,394 to Kinney; U.S. Pat. No. 3,276,944 to Levy; U.S. Pat. No. 3,502,538 to Peterson; U.S. Pat. Nos. 3,502,763 and 3,509,009 to Hartmann; U.S. Pat. No. 3,542,615 to Dobo et al. and U.S. Pat. No. 3,692,618 to Dorschner et al, the disclosures of which are incorporated herein by reference in their entirety. Both the melt-blowing and spunbonding processes can be used to produce fibers having a diameter of about 100 nanometers. Polymers that are suitable for use in the melt-blowing and spunbonding processes which can be used to form the expandable structures include, but are not limited to polypropylene, polyethylene, polybutylene terephthalate, Nylon 6, Nylon 11, polycarbonate, polyurethanes, polyesters, poly(vinylidenefluoride) and poly(ester-amides).

Once formed, the expanded member can be attached to an elongated catheter shaft by any conventional and suitable techniques so as to be in fluid communication with an inflation lumen. Similarly, the expandable member can be folded or collapsed using known and suitable techniques for assembly, packaging, delivery and deployment as is known in the art.

The following examples are presented in order to more fully illustrate certain embodiments of the invention. These examples in no way, however, should be construed as limiting the broad scope of the invention. One skilled in the art can readily devise many variations and modifications of the principles disclosed herein without departing from the scope of the invention.

EXAMPLES

Figure 9:
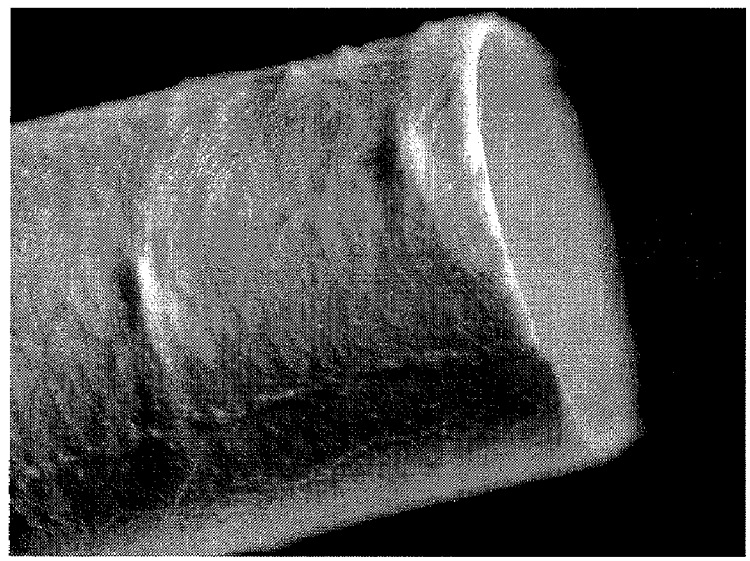
FIGS. 9 and 10 are images of the electrospun foam conduit formed in accordance with the present invention.

Example A 2 wt % high inherent viscosity Poly(L-lactide) PLLA in hexafluoroisopropanol was electrospun utilizing voltages of +10 kV (nozzle) and −10 kV (mandrel), a flow rate of 1 mL/hr, over a distance of 10 cm onto a 4.0 mm stainless steel mandrel rotating at 3000 rpm. This PLLA fiber composite in the shape of a tube with a 4.0 mm inner diameter was then annealed at 45° C. overnight in a vacuum oven to remove residual solvent and induce crystallinity. A macroscale image of the foam conduit is shown in FIG. 9.

Example B

Figure 10:
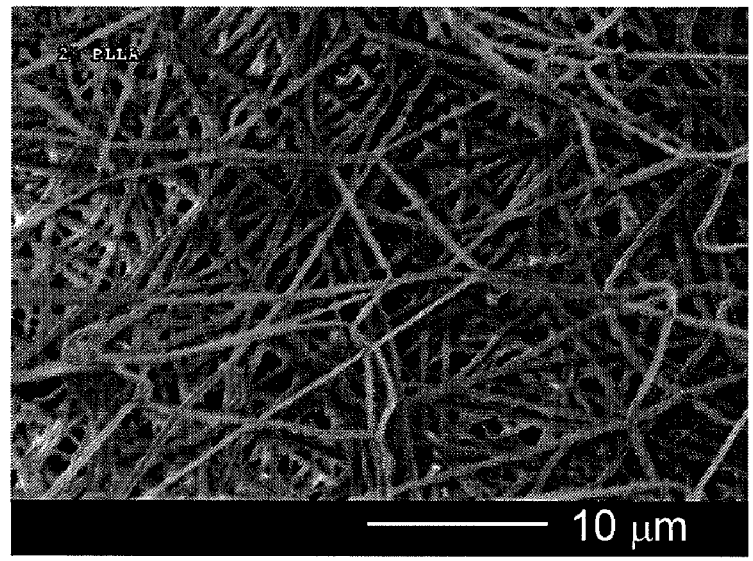

The PLLA electrospun tube segment formed in Example A was cut and placed on carbon tape, sputter coated with gold-palladium and then imaged by scanning electron microscopy. As shown in FIG. 10, surface morphology consists of micron and sub-micron diameter fibers layered on one another that include gaps therebetween.

Example C

A fibrous conduit may be formed from 5 wt % of poly(L-lactide-co-ε-caprolactone) (PLCL) 50-50 in hexafluoroisopropanol solution by electrospinning. The PLCL has an inherent viscosity of 3.07 dl/g and a molecular weight of 561,000. Electrospinning equipment includes a syringe pump (Harvard Apparatus PHD2200), a glove box, two power supply units (Gamma High Voltage Research), and a mandrel control stage designed and built in-house. Volumetric flow rate from the syringe pump may be approximately 1 mL/hr and the PLCL solution may be ejected through a stainless steel nozzle with a potential of approximately 12 kV. Electrospun fibers are directed toward an 0.053-inch diameter stainless steel mandrel spaced approximately 20 cm from the electrospinning nozzle and having a potential of approximately −6 kV. The mandrel may be rotated by the mandrel control stage at 1500 RPM while the electrospinning nozzle oscillates axially over 75 passes at an average linear speed of approximately 12 mm/s with an inflated Pellethane balloon at a nozzle voltage of +10 kv, target voltage of −5 kV, distance of 4.0 cm, and infusion rate of 1 mL/h. The resulting fibrous conduit may be removed from the mandrel and subjected to one or more ethylene oxide sterilization cycles. The sterilization cycles cause the fibers to swell and form a fluid tight conduit (FIGS. 11a-11d).

It will be apparent to those skilled in the art that various modifications and variations can be made in the method and system of the present invention without departing from the spirit or scope of the invention. Thus, it is intended that the present invention include modifications and variations that are within the scope of the appended claims and their equivalents.

What is claimed is:

1. An intraluminal catheter device comprising:
an elongated catheter shaft having a proximal end portion and a distal end portion, the shaft having an inflation lumen disposed between the proximal end portion and the distal end portion; and
an expandable member formed essentially of an electrospun matrix of fiber elements and disposed proximate to the distal end portion of the catheter shaft to define an inner chamber fluidly coupled to the inflation lumen, wherein individual fiber elements of the matrix carry at least one therapeutic agent.

2. The device of claim 1, wherein the fiber elements comprise a polymer.

3. The device of claim 2, wherein the at least one therapeutic agent is incorporated into the polymer of the individual fiber elements.

4. The device of claim 3, wherein the at least one therapeutic agent is dispersed and encapsulated in the polymer of the individual fiber elements.

5. The device of claim 2, wherein the polymer is selected from the group consisting of polyamides, polyurethanes, fluoropolymers, polyolefins, polyimides, polyimines, (methyl)acrylic polymers, polyesters, and co-polymers thereof.

6. The device of claim 1, wherein the individual fiber elements each include at least one coating.

7. The device of claim 6, wherein the at least one coating includes the at least therapeutic agent.

8. The device of claim 7, wherein the individual fiber elements include a second coating surrounding the first coating, the second coating-comprising a protective substance.

9. The device of claim 8, wherein the protective substance is selected from the group consisting of glucose, hydrophilic coatings, mediums which are dissolvable in blood or aqueous mediums, and other mediums which will crack under expansion.

10. The device of claim 6, wherein the at least one coating comprises a protective substance.

11. The device of claim 1, wherein the at least one therapeutic agent is selected from the group consisting of antiproliferative, anti-inflammatory, antineoplastic, antiplatelet, anti-coagulant, anti-fibrin, antithrombotic, antimitotic, antibiotic, antiallergic and antioxidant compounds and combinations thereof.

12. The device of claim 1, wherein the expandable member is expandable from a first profile to a second profile.

13. The device of claim 1, wherein the expandable member is essentially fluid-tight and can maintain an expanded profile.

14. The device of claim 1, the expandable member defining an outer surface, and further comprising a coating on at least one portion of the outer surface of the expandable member.

15. The device of claim 14, wherein the coating comprises a protective substance.

16. The device of claim 14, wherein the coating comprises at least one therapeutic agent.

17. The device of claim 16, further comprising a second coating surrounding the first coating on at least one portion of the outer surface of the expandable member, the second coating comprising a protective substance.

18. The device of claim 1, wherein the matrix of fiber elements defines a plurality of gaps between the fibers.

19. The device of claim 1, wherein the at least one therapeutic agent is released from the individual fiber elements upon radial expansion of the expandable member.

20. The device of claim 1, wherein the at least one therapeutic agent is released from the individual fiber elements by diffusion upon expansion of the expandable member against a target area.

21. An intraluminal catheter device made by:
forming an expandable member a essentially of an electrospun matrix of fiber elements to define an inner chamber, individual fiber elements of the matrix carrying at least one therapeutic agent;
providing an elongated catheter shaft having a proximal end portion and a distal end portion, the shaft having an inflation lumen disposed between the proximal end portion and the distal end portion; and
attaching the expandable member to the distal end portion of the elongated catheter shaft with the inner chamber of the expandable member fluidly coupled to the inflation lumen.

22. The device of claim 21, wherein the fiber elements comprise a polymer.

23. The device of claim 22, wherein the at least one therapeutic agent is incorporated into the polymer of the individual fiber elements.

24. The device of claim 23, wherein the at least one therapeutic agent is dispersed and encapsulated in the polymer of the individual fiber elements.

25. The device of claim 22, wherein the polymer is selected from the group consisting of polyamides, polyurethanes, fluoropolymers, polyolefins, polyimides, polyimines, (methyl)acrylic polymers, polyesters, and co-polymers thereof.

26. The device of claim 21, wherein the individual fiber elements each include at least one coating.

27. The device of claim 26, wherein the at least one coating includes the at least one therapeutic agent.

28. The device of claim 27, wherein the individual fiber elements include a second coating surrounding the first coating, the second coating comprising a protective substance.

29. The device of claim 26, wherein the at least one coating comprises a protective substance.

30. The device of claim 21, wherein the at least one therapeutic agent is released from the individual fiber elements upon radial expansion of the expandable member.

31. The device of claim 21, wherein the at least one therapeutic agent is released from the individual fiber elements by diffusion upon expansion of the expandable member against a target area.

* * * * *